United States Patent [19]

Penman et al.

[11] Patent Number: 4,569,916

[45] Date of Patent: Feb. 11, 1986

[54] ASSAY FOR TUMOR PROMOTING AGENTS

[75] Inventors: Sheldon Penman, Brookline; Edward G. Fey, Boston, both of Mass.

[73] Assignee: Massachusetts Institute of Technology, Cambridge, Mass.

[21] Appl. No.: 612,233

[22] Filed: May 21, 1984

[51] Int. Cl.[4] .................. C12N 15/00; C12Q 1/02; C12R 1/91

[52] U.S. Cl. .................. 436/64; 435/29; 435/172.1; 435/948

[58] Field of Search .................. 436/63, 64, 813; 435/29, 32, 172.1, 240, 948, 6

[56] References Cited

PUBLICATIONS

Hay et al. (eds.), *Amer. Type Culture Collection, Catalogue of Strains II*, 4th ed., 1983, pp. 92 and 144.
Ohuchi et al., *Prostaglandins*, vol. 15, No. 4, p. 723, 1978.
Elias et al., *J. Invest. Dermatology*, vol. 62, No. 6, pp. 569–581, 1974.
Manger et al., *Cancer Res.*, vol. 42, pp. 4591–4599, 1982.
Colburn et al., *Cancer Res.*, vol. 38, pp. 624–634, 1978.
Borenfreund et al., *Ann. N.Y. Acad. of Sciences*, vol. 349, pp. 357–371, 1980.
de Serres et al., (eds.), *Chemical Mutagens*, vol. 6, 1971.
Altenburg et al., *Cancer Res.*, vol. 36, pp. 251–257, 1976.
Berwald et al., *J. Natl. Cancer Inst.*, vol. 35, No. 4, 1965, pp. 641–657.

*Primary Examiner*—Barry S. Richman
*Assistant Examiner*—C. M. Delahunty
*Attorney, Agent, or Firm*—Arthur A. Smith, Jr.; Paul J. Cook

[57] ABSTRACT

A composition is tested to determine whether it is a tumor promoter or a complete carcinogen by exposing a stable epithelial cell line to the composition for an incubation time period sufficient to induce morphological changes in the cell line. After the incubation time, the cells are observed by morphology changes induced by the composition, which changes are compared to that caused by a known tumor promoter or a known complete carcinogen.

6 Claims, 6 Drawing Figures

ASSAY FOR TUMOR PROMOTING AGENTS

BACKGROUND OF THE INVENTION

The Government has rights in this invention by virtue of National Institute of Health grant number CA-08416 and grant number CA34017, respectively, and by virtue of National Science Foundation grant number PCM-8004696.

This invention relates to an assay process for determining whether a composition is a tumor promoting agent or has promoting activity as part of its carcinogenic action.

Tumor promoters are those compositions that effect the formation of tumors in those cells that have been previously initiated. Initiation is an event which appears to damage the DNA of cells, but does not necessarily result in tumor formation. Exposure of initiated cells to promoting agents leads to carcinomas and papillomas. Prior to the present invention, there has been no simple, short-term test for determining whether a composition is a tumor promoter or has tumor promoting activity. One existing test involves painting mouse skin with suspected compositions. Demonstration of promoting activity requires repeated application of the composition over several months before carcinomas and papillomas are detected. This analysis is expensive and time consuming.

A second category of compositions are known as complete carcinogens. These are capable of inducing tumors by themselves without the prior requirement of exposure to initiators or treatment with promoters. Such compositions appear to combine both initiating and promoting activity. All complete carcinogens tested by the assay described here have demonstrated the alteration of epithelial morphology characteristic, and thus appears to have promotional activity by the present test. Prior to the present invention, compositions to which humans are exposed such as food additives, topical products or the like must be routinely tested to determine their activity for causing cancer in humans. Long term tests for carcinogenic compositions expose animals to suspected compositions and measure tumor formation. Such tests are labor intensive, expensive and produce variable results. A widely used short-term test, that does not require animal testing, is known as the Ames test. This test is of limited utility and can only determine whether a composition damages DNA, resulting in mutagenesis. It cannot measure tumor promoting activity of compositions nor detect that activity of carcinogens which are not mutagenic. The Ames test involves the activation of a composition using a microsomal extract from rat liver. The activated composition is mixed with a bacterial strain bearing a mutation. Mutagenic compounds are detected by their ability to reverse the mutation, allowing the bacteria to grow in a restrictive medium. Thus, carcinogens are selected on the basis of their ability to induce specific mutations.

While most complete carcinogens cause mutagenesis, not all mutagens are complete carcinogens. Furthermore, the Ames test is not capable of determining whether a composition is a tumor promoter. For example, the Ames test is not capable of determining which components of tobacco smoke are tumor promoters nor can it detect the tumor promoting activity of deoxin (TCDD). Thus, the Ames test is seriously deficient, since both dioxin and tobacco smoke are well known tumor promoting agents common in the environment.

Accordingly, it would be highly desirable to provide an accurate, inexpensive and definitive short-term test for determining whether a particular composition is a tumor promoter or has tumor promoting activity. Also, this test should establish whether a known mutagen has promoter activity and is therefore likely to behave as a complete carcinogen. Furthermore, it would be desirable to provide a test which is capable of making such a determination directly at extremely low dilutions in the order of one part per billion or less.

SUMMARY OF THE INVENTION

This invention is based upon the discovery that compositions of interest which are tumor promoters or complete carcinogens significantly alter the morphological structure of certain tissue-forming epithelial cells in a specific and quanitifiable manner when the cultivated cells are exposed to these compositions, for a short time and even at extremely low dilutions. It has been found, in accordance with this invention, that tumor promoters, agents with promoting activity, or complete carcinogens alter the intermediate filament structure of the epithelial cells in a unique and characteristic manner. The intermediate filaments become markedly bundled while the cell to cell borders become deformed, separated and elongated. Concommitant with these intermediate filament and morphological alterations, the normally stationary cells become markedly motile after exposure to tumor promoters or compositions with promoting activity. It has been found that these structural deformations and induced motility occur in the absence of both protein and RNA synthesis. Thus, the alterations are independent of other biochemical responses, which might serve as markers for promotion.

All the major filament systems of epithelial cells are altered eventually by compositions with promoting activity. However, the cytokeratin network appears to be modified earliest in a characteristic and quantifiable manner. Another concomitant and quantifiable effect is the rapid conversion of the stationary cultured cell colonies into highly motile cells whose movement is easily quantified using phase microscopy and video time lapse recording. In the process of this invention, a stable, cultured epithelial cell line is exposed to a composition which may or may not be a tumor promoter, an agent with promoting activity, or a complete carcinogen. The cell culture, intact or extracted, is then observed directly to determine whether the cytokeratin network has become bundled and whether the cell to cell borders have become deformed, detached and elongated. Alternatively, it may be determined whether cell motility has been induced. If such changes occur, then the composition to which the cell line is exposed is either a tumor promoter, an agent with promoting activity, or a complete carcinogen. Observation of the cell, both prior to and after exposure to the test composition, can be effected in any of several convenient manners. These include phase contrast light microscopy with video time-lapse recording to record cell motility. Another method is the immunofluorescent staining of the cytokeratins in fixed cells. Electron microscopy of simply prepared, detergent extracted cell whole mounts offers extremely high sensitivity, although requiring somewhat more elaborate equipment. The observations may be made on intact, fixed or partially extracted cells. The compositions may be added to the cell culture directly or after prior activation by a suitable activating system.

DESCRIPTION OF SPECIFIC EMBODIMENTS

In accordance with this invention, samples of a stable epithelial cell line, growing as colonies, are exposed to compositions to be tested for their activity as a tumor promoter or as a complete carcinogen. The cells exposed to the sample composition then are observed directly to examine alterations in overall morphology, the induced motility and in cytokeratin filaments organization of the cell colonies. If the cytokeratins are characterized by being elongated, bundling and the cells disconnected, then the test composition is considered to be either a tumor promoter or a complete carcinogen. This characteristic change of the cytokeratin intermediate filament organization of the cells can be seen directly when using immunofluorescent microscopic techniques of cells extracted with a detergent such as Triton X-100 in a physiological buffer, or by transmission electron microscopy of detergent extracted whole mounts.

The induction of motility is observed by phase contrast microscopy and time-lapse video recording. The alteration of the intermediate filament framework of the cells is compared with the gross morphological changes induced by known tumor promoters or complete carcinogens such as aplysiatoxin, 12-0-tetradecanoyl phorbol-13-acetate (TPA), mezerein, or benzo(a)pyrene. A differentiated epithelial cell line such as the MDCK dog kidney tubule cell line will be used. The intermediate filament framework can be observed directly by phase contrast microscopy, immunofluorescent microscopy or whole mount electron microscopy. The intermediate filament framework of an epithelial cell colony is visualized by indirect immunofluorescent microscopy using antibody directed against intermediate filament proteins. The analysis of the isolated intermediate filament network is done after a simple procedure of detergent extraction and purification described below. This protocol allows for direct analysis of both the morphological and biochemical alterations (i.e., phosphorylation) induced by tumor promoting compositions. Alternatively, the living colonies can be viewed by a standard phase contrast microscope and the induced motility measured by the resultant cell separation.

Representative stable cell lines which can be utilized in the present invention are those which are derived from epithelia, form geometric cuboidal colonies and maintain both a constant phenotype and karyotype for at least 50 passages. One such cell line is known as MDCK and is derived from dog kidney epithelium.

In the process of this invention, a cell culture is grown until it has achieved a subconfluent density where cell colonies possess from about 20 to 200 cells, for example. Thereafter, samples of the cell culture are exposed to test compositions at varying concentrations and for varying time periods. The tested cell cultures then are observed directly to determine alterations of the intermediate filament framework of the cell such as by immunofluorescent microscopy or whole mount electron microscopy or phase contrast microscopy combined with time-lapse video recording. Those test samples which showed bundling of the intermediate filament framework, separation and elongation of the cell to cell wall or induced cell motility are characteristic of test compositions which are either tumor promoters or complete carcinogens. The terms "filament bundling" and "cell elongation" and "induced motility" will become more apparent with reference to the examples and the accompanying figures.

DESCRIPTION OF THE FIGURES

FIG. 5. Immunofluorescence micrographs of MDCK colonies extracted with nonionic detergent and stained for cytokeratins. MDCK colonies were treated for 2 hours with 20 $\mu$g/ml colchicine (a) or 5 $\mu$g/ml cytochalasin D (c). Colchicine had no effect on the organization of cytokeratins in the cell colonies while cytochalasin D treatment produced a diffuse staining pattern, which is very different from the morphological signatures of promoters. When 5 ng/ml TPA was added for 2 hours to cells previously treated with colchicine (b) the cytokeratin pattern observed is characteristic of cells treated with TPA alone (FIG. 1h). When TPA (5 ng/ml) was added for 2 hours to cells exposed to cytochalasin D (d) a striking stellate keratin fluorescence is observed. This pattern displays the formation of keratin bundles and cell spreading characteristic of tumor promoters, but the signature is clearly different from that induced by TPA alone. (200×).

The following example illustrates the present invention and is not intended to limit the same.

EXAMPLE I

Cell Culture

Madin Darby canine kidney (MDCK) cells were grown in Dulbecco medium supplemented with 10% fetal calf serum at 37° C. in an atmosphere containing 5% carbon dioxide and used at a subconfluent density of $6-8 \times 10^6$ cells/100 mm diameter plastic tissue culture plate. Dimethyl sulfoxide or acetone was added to control plates at a concentration of 0.1%. Tumor promoters and other compounds were added at concentrations described with reference to the figures. The S9 mixture consisted of (final concentration) 33 mM Kcl, 8 mM $MgCl_2$, 5 mM glucose-6, -phosphate, 4 mM TPN, 10 mM $NaHPO_4$ (pH 7.4) in 2 ml Dulbecco's with 0.3 ml rat liver $9,000 \times g$ supernatant.

Cell Fractionation

Madin Darby canine kidney (MDCK) listed kidney tubule cell line colonies, grown on plastic plates or glass coverslips were rinsed twice with phosphate buffered saline, extracted with cytoskeleton buffer (CSK); 100 mM NaCl, 300 mM sacrose, 10 mM PIPES (pH 6.8), 3 mM $MgCl_2$, 0.5% Triton X-100 and 1.2 mM PMSF) and the supernatant was removed as the 'soluble' fraction. The 'cytoskeleton' fraction was obtained after incubation in an extraction buffer (identical to CSK with 250 mM $(NH_4)_2SO_4$ in place of NaCl) for 10' at 0° C. The 'chromatin' fraction was obtained after a 20' digestion at 20° C. in CSK buffer with 50 mM NaCl containing 400 μg/ml bovine puncreatic DNAse I/EC 3.1.4.5, Worthington) and 400 μg/ml pancreatic RNAase A/EC 3.1.4.22, Sigma) followed by a 5' incubation in 250 mM $(NH_4)_2SO_4$ (final concentration). The remaining insoluble structure is the cytoskeleton.

Phase Microscopy

Time-lapse video micrographs of line MDCK colonies were obtained using phase-contrast optics on a Zeiss Universal microscope coupled to a RCA Nuvicon TC 1005 video camera.

Immunofluorescence Microscopy

Immunofluorescence microscopy of the cytoskeleton fractions was performed using cell colonies grown on glass coverslips. Cytoskeletons were prepared from these colonies as described above, and fixed in 3.7% formaldehyde for 30 minutes at 0° C. Fixed cytoskeletons were extensively washed in phosphate buffered saline (PBS). Antibodies to cytokeratins were applied at 1:100 dilution in PBS and coverslips were incubated 30 minutes at 37° C. After extensive washing in PBS, the cytoskeletons were incubated with goat anti-rabbit IgG labeled with tetramethyl-rhodamine isothiocyanate at a dilution of 1:40 for 30 minutes at 37° C. The labeled fractions were washed in PBS, mounted and photographed using epifluorescence.

(The rabbit antikeratin antibody was diluted 1:40 in phosphate buffered saline (PBS) and incubated with fixed cells or cell fractions for one hour at 37° C. The cells were washed extensively in PBS and incubated with a goat antirabbit antibody to which tetramethyrhodamine isothiocyamite had been covalently attached. The second antibody was incubated with the cells for one hour at 37° C. The cells of cell fraction were washed extensively, mounted on microscope and photographed under epifluorescent illumination).

Electron Microscopy

Whole mount transmission electron microscopy was done on MDCK colonies grown on gold grids previously coated with formvar and carbon. Cytoskeleton fractions were prepared as described above, fixed in 2.5% gluteraldehyde, post-fixed in 1% $OsO_4$ and dehydrated through an ethanol series. The grids were dried through the $CO_2$ critical point and coated with gold palladium using established prior art methods prior to examination in a JEM 100B transmission electron microscope.

Alternatively, a further extraction is performed. The cytoskeleton is exposed to 0.25M $(NH_4)_2SO_4$, then 100 μg/ml of pancreatic DNAse and finally 0.25M $(NH_4)_2SO_4$ again. The preparation is then processed exactly as above.

Results

Figure 1:
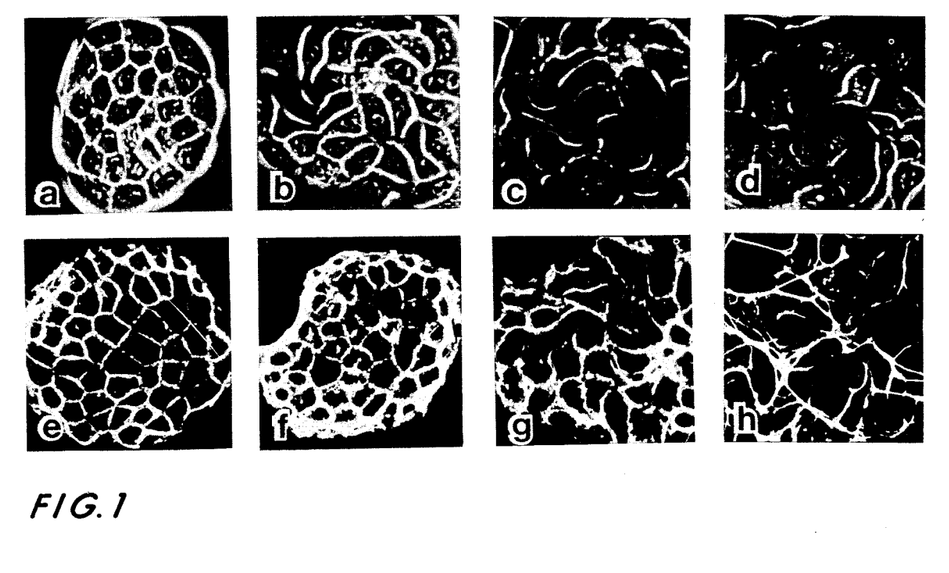
FIG. 1. Video time-lapse micrographs (a–d) showing the progression of morphological alterations induced in a living MDCK cell colony after exposure to 5 ng/ml TPA. These phenotypic changes are faithfully retained in detergent extracted cells (e–h) stained from keratins and visualized by immunofluorescence microscopy. The control colonies (1a and e) show typical epitheloid morphology which is seen to deform at 30' (b and f). At 1 hour (c and g) cytoplasmic processes and cytokeratin bundles develop. These become the predominant feature after 2 hours (d and h). (200×).

The gross morphological alterations produced by 5 ng/ml TPA are shown in FIG. 1. FIGS. 1a–d is a time course of morphological changes observed on living MDCK colonies using phase micrographs taken from time-lapse video recordings. The control MDCK colony (FIG. 1a) represents a typical 30 cell epithelial colony which displays a tight cuboidal morphology. After 30 minutes in TPA (FIG. 1b) the colony has enlarged, and the cells have become flattened and elongated. After 1 hr incubation in TPA (FIG. 1c), the cells have elongated and developed crescent-shaped processes which become more pronounced as the now motile cells move apart. At 2 hrs (FIG. 1d), the long cellular processes have become a predominant feature of the cell morphology and the MDCK cells display a morphological 'signature' which is a characteristic response unique to tumor promoting agents.

The images shown in FIGS. 1e–h are derived from MDCK colonies from a time course identical to that shown in FIGS. 1a–d. In this case, the cells were extracted at each time point and nuclear matrix-intermediate filament preparations were prepared in situ. These structures retain only 5% of the original cell proteins and are devoid of nucleic acids and phospholipid. The NM-IF prepations are stained using a double antibody immunofluorescence technique where the first antibody is to keratin proteins. These images represent, therefore, the distribution of cytokeratin filaments after exposure to TPA. In the control colony (FIG. 1e), the cuboidal morphology is apparent in the keratin filaments which are concentrated at the regions of intercellular junctions. As the morphological signature develops in response to TPA, the distribution of the cytokeratin filaments is altered in a manner which closely parallels the formation of cellular processes observed in the intact cells. Thus the pattern of cytokeratin distribution in the NM-IF preparation may be used to monitor the morphological changes induced by TPA.

Figure 2:
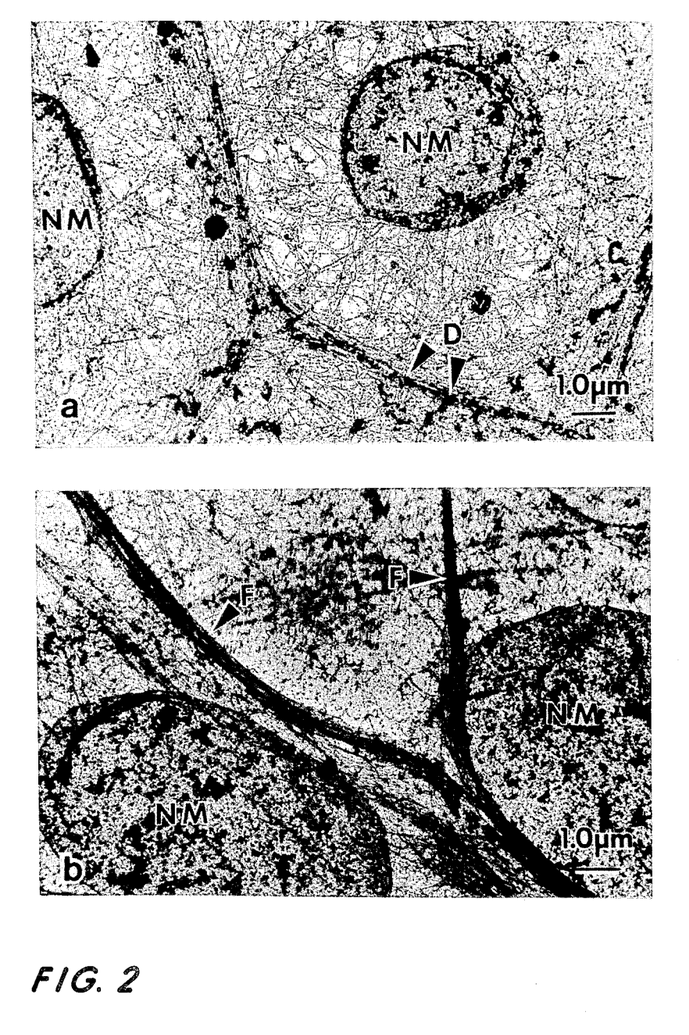
FIG. 2. Transmission electron micrographs of cytokeratin networks derived from detergent and salt extracted whole mount preparations of MDCK epithelial colonies. Control MDCK colonies, depleted of soluble protein, phospholipid and nucleaic acids (a) retain cell borders with residual desmosomes (D). The nuclear matrices (NM) are located in the center of the cell and associated with a fine web of intermediate filaments. After exposure to 5 ng/ml TPA for 2 hours (b) the nuclear matrices (NM) have become enlarged and distorted. The web of individual filaments has been replaced by dense filament bundles (F) which are closely associated with the nuclear matrix structures.

More detailed examination of the alterations in NM-IF organization in response to TPA or the promoting agents is facilitated by the use of whole mount transmission electron microscopy. FIG. 2 shows the detailed organization of the control NM-IF scaffold. The chromatin depleted nuclear matrix is observed in association with cytokeratin filaments which terminate at residual desmosomal structures. After 2 hrs exposure to 5 ng/ml TPA, the ordered arrangement of filaments in the control NM-IF scaffold is drastically altered (FIG. 2b). The filaments which are normally distributed in a well spread, radial pattern now form dense bundles. The distorted nuclear matrices become elongated and enlarged and are observed in close association with the newly formed filament bundles (FIG. 2b).

Figure 3:
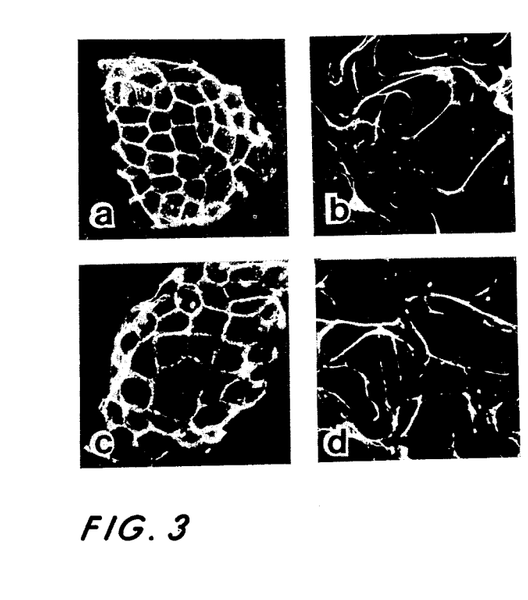
FIG. 3. Immunofluorescent micrographs of MDCK colonies extracted with nonionic detergent and stained for cytokeratins. Protein and RNA synthesis was inhibited for 30' with 5 $\mu$g/ml cycloheximide (a) or 5 $\mu$g/ml actinomycin D (c) prior to extraction and fixation. Neither drug altered the epithelial morphology of MDCK colonies (compare with FIG. 1e). When 5 ng/ml TPA was subsequently added to the MDCK colonies pretreated with cycloheximide (b) or actinomycin D (d) and incubated for 2 hrs, the morphological signature characteristic of TPA treatment alone was observed (compare with FIG. 1h). (200×).

That the morphological alterations included by TPA may represent a primary response to the tumor promoter is suggested by the experiment described in FIG. 3. MDCK colonies were treated with either 5 µg/ml cycloheximide (FIG. 3a) or 5 µg/ml actinomycin D (FIG. 3c) for 30 minutes. The inhibition of protein and RNA synthesis does not alter the morphology of the MDCK colonies which are indistinguishable from control colonies (FIG. 1e). When drug treated colonies are subsequently exposed to 5 ng/ml TPA, the characteristic morphological response to tumor promoters is observed (FIGS. 3b and d). This response to TPA is independent of gene expression de novo and is therefore distinguishable from those biochemical markers of tumor promotion which require protein and/or RNA synthesis.

Figure 4:
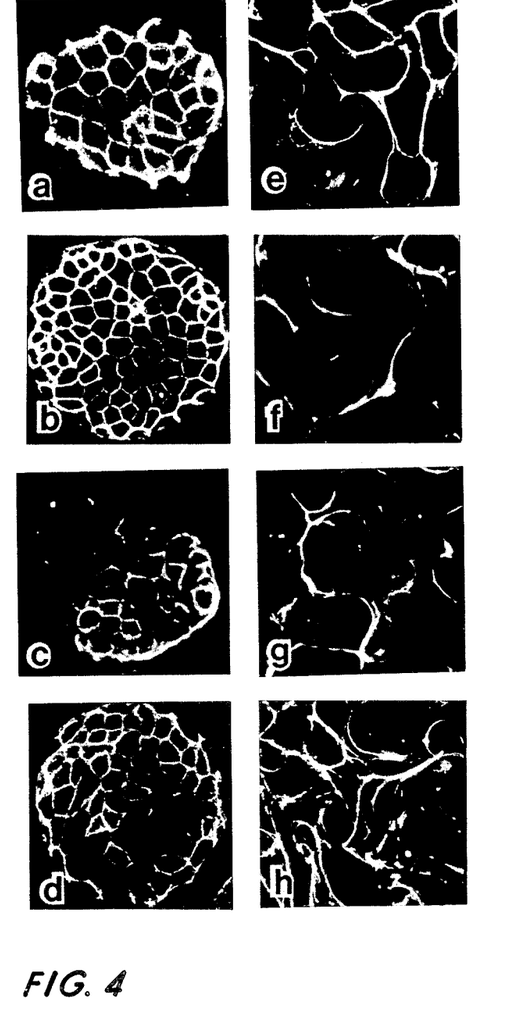
FIG. 4. Immunofluorescence micrographs of nonionic detergent extracted MDCK colonies and stained for cytokeratins. MDCK colonies were treated with the following non-promoting compounds for 2 hours, then extracted colonies were stained with antikeratin; (a) 10 ng/ml 4$\alpha$phorbol-12,13-didecanoate, (b) 20 ng/ml phorbol, (c) 100 ng/ml EGF and (d) 1 $\mu$g/ml A23187. None of these compounds caused any significant alteration of epithelial morphology. The addition of the following tumor promoters: (e) 5 ng/ml mezerein, (f) 5 ng/ml aplysiatoxin, (g) 5 ng/ml teleocidin and (h) 20 $\mu$g/ml benzoyl peroxide all produced a morphological signature which is characteristic of that produced by TPA. (200×).

The morphological signature induced in MDCK epithelia by TPA is characteristic for all tumor promoters examined. The micrographs shown in FIG. 4 compare the effects of a variety of agents. The non-promoting, or weak first-stage promoting phorbol compounds, 4αphorbol-12,13-didecanoate and phorbol have no detectable effect on MDCK morphology (FIGS. 4a and b). In addition to mitogen, epidermal growth factor and the hyperplastic calcium ionsphore A23187, both agents which mimic some biochemical aspects of promotion, do not affect MDCK morphology (FIGS. 4c and d). In contrast, a wide variety of compounds, shown to be complete or second-stage promoters in vivo induce flattened morphologies with cytokeratin rich processes which are indistinguishable from the morphological signature induced by TPA. The promoters examined are mezerein (FIG. 4e), aplysiatoxin (FIG. 4f), teleocidin (FIG. 4g), and benzoyl peroxide (FIG. 4h). These compounds constitute a broad range of structurally unrelated tumor promoting agents and all produce very similar lesions in NM-IF organization of these epithelial colonies.

Figure 5:
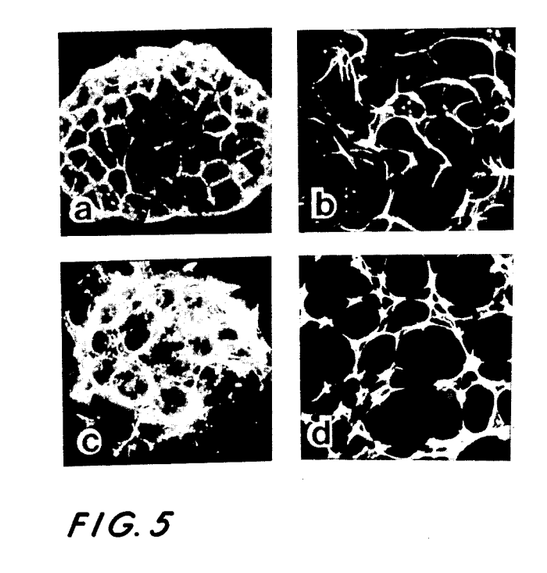

To determine whether the microtubule or microfilament networks were involved in the altered morphology induced by tumor promoters, MDCK colonies were incubated in either colchicine or cytochalasin D for 2 hrs. As is apparent in FIG. 5a colchicine treatment causes no change in epithelial colony organization. If TPA (5 ng/ml) is added, after prior incubation in colchicine the morphological signature characteristic of tumor promoters is observed (FIG. 5b), indicating that the microtubule system is not directly involved in the morphological response to tumor promoters. The effect cytochalasin D is somewhat more complex. After a 2 hour exposure to cytochalasin D, the morphology of the MDCK colonies is severely altered (FIG. 5c). However, the resultant morphology is clearly different from that produced by tumor promoters. The colonies remain in tight clusters while there is a partial breakdown of intercellular association. The major characteristics of induced changes by tumor promoters (i.e., rapid cell spreading and the formation of long, cytokeratin-rich filament bundles) are not observed in response to cytochalasin D. When TPA is added to MDCK colonies previously exposed to cytochalasin D (FIG. 5d) both cell spreading and process formation are observed. The morphological signature which results from a combination of cytochalasin D and TPA is a striking stellate pattern clearly different from that induced by TPA alone. This result suggests that while TPA does induce cytokeratin process formation and cell spreading, associations with the microfilament network may influence the alteration of cytokeratin organization induced by TPA and other tumor promoters.

Figure 6:
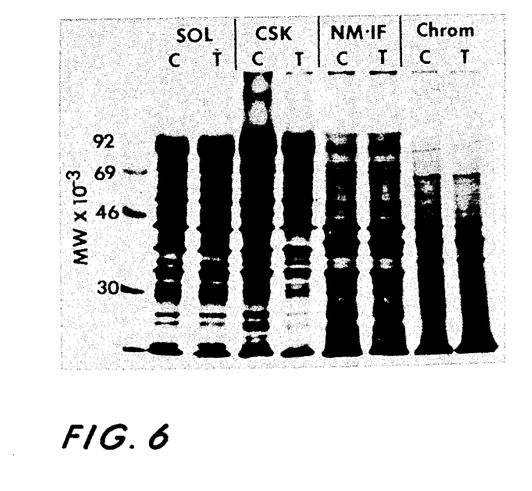
FIG. 6. Immunofluorescent micrographs of NM-IF scaffolds derived from MDCK colonies and stained for cytokeratins. MDCK colonies were treated for one hour with a standard S9 microsomal activation mixture (see below) (S9). The S9 mixture contained 10 μg/ml 2 acetylaminofluorene (2AAF), 10 μg/ml dimethylbenzanthracene (DMBA), and 10 μg/ml benzo(a)pyrene (BAP). The S9 mixtures and carcinogens were removed and the cells were incubated in Dulbecco's MEM with 10% fetal bovine serum for 12 hours prior to extraction and immunofluorescent staining. The S9 mixture did not alter the morphology or intermediate filament structure of the colony, while dramatic alterations of both were observed in the presence of the three complete carcinogens. The carcinogens also induced motility in the MDCK cells.

In the experiment described in FIG. 6, total cell protein was labeled with $^{35}$S methionine 24 hours prior to incubation with TPA. After incubation with 5 ng/ml TPA for 2 hours, the MDCK colonies were fractionated to the NM-IF structure and proteins present in each of the 4 fractions were analyzed on 10% polyacrylamide gels. As is clear from FIG. 6, the distribution of proteins among the four cellular subfractions was virtually unchanged by exposure to TPA. This result suggests that morphological changes induced by TPA result from reorganization and not disruption of cytoskeletal elements.

As described in this example, a number of structurally unrelated compounds known to promote tumors in vivo are shown to induce a rigid breakdown of epithelial tissue organization which results in a characteristic morphological signature in MDCK epithelial colonies. The epitheliod nature of these cuboidal cell colonies is altered and individual cells become motile, flattened and elongated. The predominant aspects of altered morphology in these promoter treated cells are reflected in the distribution of cytokeratins in the nuclear matrix-intermediate filament scaffold, a structure depleted of nucleic acids, phospholipid and 95% of the total cell protein. As shown in FIG. 1, the morphological alterations observed in intact cell colonies (FIGS. 1a-d) are preserved with great fidelity by the cytokeratin filaments in the extracted NM-IF structures (FIGS. 1e-d). Examination of NM-IF scaffolds using whole mount transmission electron microscopy (FIG. 2) indicates that the elongation and flattening of MDCK cells after exposure to tumor promoters is reflected by a breakdown of cell borders and bundling of the cytokeratin filaments along the axis of cell elongation. The generality of morphological response to tumor promoters is demonstrated in FIG. 4. Five structurally unrelated compounds, all known to be complete or second stage tumor promoters are shown to induce identical morphological signatures after exposure to the promoting agent for 2 hours. Putative first stage promoters or nonpromoting analogues to TPA have no effect on MDCK morphology.

FIG. 3 demonstrates that the morphological changes induced by tumor promoting agents occur, with no change in rate or extent, in the absence of both protein and RNA synthesis. Two generally accepted markers for tumor promoting activity in vitro are the induction of plasminogen activator (PA) and prostoglandins. Previous studies have shown that both of these effects require continued protein or RNA synthesis. The results presented here suggest that the morphological changes resulting from exposure to tumor promoters are independent of either PA release or prostaglandin stimulation. A third biochemical marker normally associated with tumor promotion is the release of fibronectin from cell surfaces. As this protein in either not present or present only in minute amounts in both normal and transformed epithelical cells the relevance of this marker to promotion in this system in unclear. Ornithine decarboxylase (ODC) is another biochemical marker for tumor promotion, although its significance is questionable. ODC induction by tumor promoters is inhibited by colchicine a compound which does not block the morphological alterations induced by tumor promoters. While it is possible to separate tumor promotion from mitogenesis using selected cell systems, both tumor promoters and mitogens have been shown to elicit similar results in a number of systems. Epidermal growth factor (FIG. 4c) and other growth hormones cause no morphological alterations and are therefore separable from tumor promoters in their effects on epithelial cytoarchitecture.

The cytokeratin intermediate filament system is proposed as a possible target for tumor promoter activity on cytoskeletons. This is suggested by the experiments shown in FIG. 5.

Depolymerization of microtubules has no effect on MDCK colony morphology or their subsequent responce to TPA. Cytochalasin D does have a pronounced effect, however the bundling of keratins and the extensive cell spreading, characteristic of tumor promoters, still occur in response to TPA. This suggests that at least part of the keratin reorganization is independent of microfilament function.

We observed (FIG. 6) that the distribution of proteins between soluble and structural compartments is largely unaltered by tumor promoting agents. This result suggests that the action of tumor promoters does not involve a breakdown of structural elements but rather a spatial reorganization of cellular elements whose connectedness remains unchanged.

The results presented in this study show that tumor promoters act by a common mechanism involving the reorganization of the nuclear matrix-intermediate filament network. These observations provide a rapid and reliable assay for tumor promoters in an epithelial system and establish a basis from which the mechanism of tumor promoter action on cytoskeletal elements may be more completely understood.

We claim:

1. A test process for identifying a composition of interest as being within the class consisting of tumor promoters, agents having tumor promoting activity, and complete carcinogens, said test process comprising the steps of:
    exposing an epithelial cell line to the composition of interest for a predetermined time period; and
    detecting a morphological change within said exposed epithelial cells by observation of said exposed cells and comparison of morphological changes therein with those of an unexposed epithelial cell control, said morphological change comprising bundling of the cytokeratin filaments within said cells, the occurrence of said morphological change identifying the composition of interest as being within the class.

2. The process of claim 1 wherein said morphological change further comprises elongation of the cell walls and cell motility.

3. The process of claim 1 wherein said epithelial cell line is a Madin Darby canine kidney cell line.

4. The process of any one of claims 1 or 3 wherein said cell line is observed directly by immunofluorescent microscopy.

5. The process of any one of claims 1 or 3 wherein said cell line is observed directly by whole mount electron microscopy.

6. The process of any one of claims 1 or 3 wherein said cell line is observed directly by time lapse recording means.

* * * * *